US009662300B2

(12) United States Patent
Hassan et al.

(10) Patent No.: US 9,662,300 B2
(45) Date of Patent: May 30, 2017

(54) SOLID NAPROXEN CONCENTRATES AND RELATED DOSAGE FORMS

(71) Applicant: Pharmaceutics International, Inc., Hunt Valley, MD (US)

(72) Inventors: EmadEldin M. Hassan, Parkton, MD (US); Sridhar Gumudavelli, Cockeysville, MD (US)

(73) Assignee: Pharmaceutics International, Inc., Hunt Valley, MD (US)

( * ) Notice: Subject to any disclaimer, the term of this patent is extended or adjusted under 35 U.S.C. 154(b) by 0 days.

(21) Appl. No.: 14/095,593

(22) Filed: Dec. 3, 2013

(65) Prior Publication Data

US 2014/0093562 A1    Apr. 3, 2014

Related U.S. Application Data

(63) Continuation of application No. 13/727,264, filed on Dec. 26, 2012, now abandoned, which is a continuation of application No. 12/547,329, filed on Aug. 25, 2009, now abandoned.

(51) Int. Cl.
*A61K 31/192* (2006.01)
*A61K 9/48* (2006.01)
*A61K 9/16* (2006.01)

(52) U.S. Cl.
CPC .......... *A61K 9/4833* (2013.01); *A61K 9/1617* (2013.01); *A61K 9/1688* (2013.01); *A61K 9/4866* (2013.01); *A61K 31/192* (2013.01)

(58) Field of Classification Search
None
See application file for complete search history.

(56) References Cited

U.S. PATENT DOCUMENTS

| | | |
|---|---|---|
| 4,593,044 A | 6/1986 | Metz |
| 4,736,067 A | 4/1988 | Bugaut et al. |
| 4,944,949 A | 7/1990 | Story et al. |
| 5,053,533 A | 10/1991 | Giordano et al. |
| 5,206,262 A | 4/1993 | Donati et al. |
| 5,637,320 A | 6/1997 | Bourke et al. |
| 5,756,125 A | 5/1998 | Desai |
| 5,854,226 A | 12/1998 | Penkler et al. |
| 6,165,506 A | 12/2000 | Jain et al. |
| 6,383,515 B2 | 5/2002 | Sawyer et al. |
| 2007/0003611 A1 | 1/2007 | Liu et al. |
| 2007/0184100 A1 | 8/2007 | Hassan et al. |
| 2009/0104236 A1 | 4/2009 | Hassan |

FOREIGN PATENT DOCUMENTS

| | | |
|---|---|---|
| WO | WO 2006/096580 A1 | 9/2006 |
| WO | WO 2009/052251 A1 | 4/2009 |

OTHER PUBLICATIONS

European Search Report and Written Opinion issued in European Application No. EP 10 17 4052, mailed Nov. 25, 2010.

*Primary Examiner* — David J Blanchard
*Assistant Examiner* — Sarah Chickos
(74) *Attorney, Agent, or Firm* — Leydig, Voit & Mayer, Ltd.

(57) ABSTRACT

The invention provides a composition consisting essentially of a solid naproxen concentrate, wherein the solid naproxen concentrate comprises (a) a solid naproxen free acid and (b) a solid naproxen alkali salt, and wherein at least 90% of the weight of the solid naproxen concentrate is naproxen free acid and naproxen alkali salt, as well methods of producing such a solid naproxen concentrate.

26 Claims, No Drawings

SOLID NAPROXEN CONCENTRATES AND RELATED DOSAGE FORMS

CROSS-REFERENCE TO RELATED APPLICATIONS

This patent application is a continuation of copending U.S. patent application Ser. No. 13/727,264, filed Dec. 26, 2012, which is a continuation of U.S. patent application Ser. No. 12/547,329, filed Aug. 25, 2009, which is incorporated by reference.

BACKGROUND OF THE INVENTION

The success in treating most diseases mainly is governed by optimizing the rate of drug release and its delivery to the site of action. Diseases that cause pain are typical cases where the rate of drug release has a direct impact on patient health and patient quality of life. For example, while immediate drug release is required to treat fever, migraine headache, or acute dental pain, a controlled release of the same medicine would be a better choice for patients with chronic inflammatory diseases, such as rheumatoid arthritis and osteoarthritis.

Naproxen, (S)-6-methoxy-α-methyl-2-naphthaleneacetic acid and d-2-(6-methoxy-2-naphthyl)propionic acid, is one of the most effective agents in the management of acute and chronic pain and inflammatory diseases. Pharmacologically, naproxen is classified as a non-steroidal anti-inflammatory drug (NSAID). Naproxen has powerful anti-inflammatory, analgesic, and antipyretic properties.

Naproxen is used effectively in treating symptoms of rheumatoid arthritis, osteoarthritis, juvenile arthritis, ankylosing spondylitis, tendinitis, bursitis, and acute gout. Pain associated with menstrual periods, migraine headaches, and other types of mild to moderate pain also is alleviated by naproxen. Due to the efficacy and toxicity profiles of naproxen, solid and liquid naproxen delivery systems are used to satisfy a wide range of medical needs.

Naproxen can be delivered in immediate release dosage forms by enhancing the rate of dissolution via solubilization, complexation, particle size reduction, or solid dispersion techniques, whereas controlled release forms have been formulated using lipid or polymeric matrix techniques.

For immediate release dosage forms, improved water solubility of the poorly water-soluble naproxen free acid has been achieved by forming solid potassium or sodium salts. Other solid salts of naproxen with water-soluble basic compounds such as lysine (see, e.g., U.S. Pat. No. 4,593,044) or N-(2-hydroxyethyl)pyrrolidine (see, e.g., U.S. Pat. No. 5,206,262) have been described. These techniques provide solid salts with high water solubility; however, these techniques introduce unnecessary electrolytes or diminish the drug solubility in other commonly used, less hydrophilic solvents, such those used to manufacture soft gelatin capsules.

Solubilization techniques to prepare naproxen liquid solutions have been achieved using surfactants (see, e.g., U.S. Pat. No. 4,944,949) or by using surfactant-like salts of organic acids (see, e.g., U.S. Pat. No. 6,383,515). These methods, however, cannot be used in formulating tablets or powder filled capsules.

U.S. Pat. No. 5,854,226 solubilized naproxen as part of solid inclusion complexes with different cyclodextrins. However, the need to use large amounts of cyclodextrin (which can reach up to 50% of the drug concentration) and the concern of cyclodextrin toxicity make it impractical to use this approach with a high-dose drug, such as naproxen.

Particle size reduction to the nano-scale, along with alkalis and a polymeric stabilizer, also results in improved naproxen solubility (see, e.g., U.S. Pat. No. 6,165,506). However, nano-sized drug particles inherently are unstable and tend to aggregate to reduce the high surface energy generated during size reduction.

In view of the foregoing limitations of naproxen formulations, there remains a need for oral naproxen products with higher drug concentrations, as well as methods of manufacturing the oral naproxen products.

BRIEF SUMMARY OF THE INVENTION

The invention provides a pharmaceutical composition consisting essentially of a solid naproxen concentrate, wherein the solid naproxen concentrate comprises (a) a solid naproxen free acid and (b) a solid naproxen alkali salt, and wherein at least 90% of the weight of the solid naproxen concentrate is naproxen free acid and naproxen alkali salt.

The invention also provides a pharmaceutical formulation comprising (a) a solid naproxen concentrate, wherein the solid naproxen concentrate comprises a solid naproxen free acid and a solid naproxen alkali salt, and wherein at least 90% of the weight of the solid naproxen concentrate is naproxen free acid and naproxen alkali salt; and (b) a pharmaceutically acceptable carrier.

In one embodiment, the invention provides a method of manufacturing a solid naproxen concentrate, wherein at least 90% of the weight of the naproxen concentrate is naproxen free acid and naproxen alkali salt, comprising (a) mixing a naproxen alkali salt with at least one acidic substance to form a composition; and (b) optionally drying the composition to produce a solid naproxen concentrate.

In another embodiment, the invention provides a method of preparing a soft gelatin capsule formulation comprising (a) providing a solid naproxen concentrate comprising a solid naproxen free acid and a solid naproxen alkali salt, wherein at least 90% of the weight of the solid naproxen concentrate is naproxen free acid and naproxen alkali salt; (b) dissolving the solid naproxen concentrate in a soft gelatin capsule vehicle to form a soft gelatin fill; and (c) encapsulating the soft gelatin fill in a soft gelatin capsule; thereby preparing a soft gelatin capsule formulation.

Additionally, the invention provides a composition consisting essentially of a solid naproxen concentrate, wherein the solid naproxen concentrate comprises (a) a solid naproxen free acid and (b) a solid naproxen alkali salt, and wherein at least 90% of the weight of the solid naproxen concentrate is naproxen free acid and naproxen alkali salt, wherein the naproxen free acid is produced from a solid naproxen alkali salt using at least one acidic substance.

DETAILED DESCRIPTION OF THE INVENTION

The invention provides a highly concentrated naproxen composition in the solid state (herein referred to as a solid naproxen concentrate), as well as a process of manufacturing the composition. The composition (e.g., pharmaceutical composition) can consist essentially of a solid naproxen concentrate, wherein the solid naproxen concentrate comprises (a) a solid naproxen free acid and (b) a solid naproxen alkali salt, and wherein at least 90% (e.g., at least about 92%, at least about 95%, at least about 97%, at least about 98%, or at least about 99%) of the weight of the solid naproxen concentrate is naproxen free acid and naproxen alkali salt.

The solid naproxen concentrate comprises (a) a solid naproxen free acid, and (b) a solid naproxen alkali salt. The naproxen free acid and naproxen alkali salt may be present in any suitable amount. For example, the solid naproxen concentrate can comprise about 5-95% (e.g., about 10%, about 15%, about 20%, about 25%, about 30%, about 35%, about 40%, about 45%, about 50%, about 55%, about 60%, about 65%, about 70%, about 75%, about 80%, about 85%, about 90%, and ranges thereof) solid naproxen free acid and about 5-95% solid naproxen alkali salt. Preferably, the solid naproxen concentration comprises about 15-85% solid naproxen free acid and about 15-85% solid naproxen alkali salt. Desirably, the solid naproxen concentration comprises an acid to alkali salt ratio of about 50% to about 80%.

The solid naproxen free acid can be generated by any suitable process, such as from naproxen alkali salt during the process of granulation or as a result of an in-situ reaction of naproxen alkali salt with at least one de-ionizing agent. The de-ionizing agent preferably is an acidic substance. Acidic substances (herein referred to as "acids") include, but are not limited to, pharmaceutically acceptable organic or inorganic acids, hydroxyl-acids, amino acids, Lewis acids, mono- or di-alkali or ammonium salts of molecules containing two or more acid groups, and monomers or polymeric molecules containing at least one acid group. Examples of suitable acid groups include carboxylic, hydroxamic, amide, phosphates (e.g., mono-hydrogen phosphates and di-hydrogen phosphates), sulfates, bi-sulfites, and other acidic groups that are proton donors, electron acceptors, or have a pKa lower than that of naproxen.

In particular, the acids are organic acids with 2-18 carbon atoms, including, but not limited to, short, medium, or long chain fatty acids, hydroxyl acids, inorganic acids, amino acids, and mixtures thereof. Preferably, the acid is selected from the group consisting of lactic acid, gluconic acid, citric acid, tartaric acid, hydrochloric acid, phosphoric acid, nitric acid, sulfuric acid, maleic acid, monosodium citrate, disodium citrate, potassium citrate, monosodium tartrate, disodium tartrate, potassium tartrate, aspartic acid, carboxymethylcellulose, acrylic polymers, methacrylic polymers, and mixtures thereof.

Any suitable amount of the solid naproxen alkali salt can be converted to solid naproxen free acid. For example, 5-95% (e.g., 10%, 20%, 30%, 40%, 50%, 60%, 70%, 80%, 90%, or ranges thereof) of the naproxen alkali salt is converted to naproxen free acid.

The solid naproxen free acid also can be prepared by conventional methods, for example, as described in U.S. Pat. Nos. 4,736,067 and 5,053,533.

The solid naproxen alkali salt can be any suitable naproxen alkali salt, such as naproxen potassium, naproxen sodium, naproxen ammonium, naproxen salts with amino acids (e.g., lysine), and mixtures thereof. Preferably, the solid naproxen alkali salt is naproxen sodium.

The solid naproxen alkali salt can be prepared by any suitable process. The solid naproxen alkali salt (e.g., naproxen sodium) also can be obtained from any suitable source, such as Sigma-Aldrich.

The solid naproxen concentrate can be formulated into any suitable oral dosage form, such liquid and solid dosage forms. Preferably, the solid naproxen concentrate is formulated into naproxen-containing suspensions, solutions, drops, syrups, two-piece hard shell capsules, soft gelatin capsules, and tablets.

The solid naproxen concentrate can be prepared by any suitable method. For example, solid naproxen free acid can be mixed with solid alkali salt using standard techniques.

Additionally, the invention provides a method of manufacturing the solid naproxen concentrate of the invention. The starting material is solid naproxen alkali salt (herein also referred to as a naproxen salt powder). The method comprises the mixing of a solid naproxen alkali salt with at least one acid. The acid can be mixed with the solid naproxen alkali salt to form a dry powder mixture. The mixing can be achieved using any suitable mixing apparatus, such as by use of common powder blenders known in the art. For example, suitable mixing apparatus include gravity-dependent mixers, such as double cone mixers or V-blenders, and mechanical enforcement mixers, such as high speed-high shear mixers (e.g., a T. K. Fielder) or low speed planetary blenders. Preferably, the powder mixture reacts in the presence of external water, a water-miscible solvent, such as ethyl alcohol, or a mixture thereof. Similarly, the reaction can progress in the presence of internal water molecules that exist in the powder mixture as hydrates of the acids or the naproxen salts.

The amount of acid added to the naproxen salt powder can be any suitable amount. In particular, the amount of acid can be about 0.05 to about 0.95 (e.g., about 0.1, about 0.2, about 0.3, about 0.4, about 0.5, about 0.6, about 0.7, about 0.8, about 0.9, and ranges thereof) mole equivalent to the amount of naproxen salt and preferably about 0.3 to about 0.6 (e.g., about 0.35, about 0.4, about 0.45, about 0.5, about 0.55, and ranges thereof) mole equivalent to the amount of naproxen salt.

An aqueous or hydro-alcoholic solution of the acid can be directly used to form the solid naproxen concentrate of the invention. The acid substance concentration in the solution is typically in the range of about 1% to about 50% (e.g., about 5%, about 10%, about 15%, about 20%, about 25%, about 30%, about 35%, about 40%, about 45%, and ranges thereof) by weight. Preferably, the acid concentration is about 5% to about 25% by weight. The acid solution is mixed or kneaded with the solid naproxen salt mixture using high or low shear mixers or granulators, which are known in the art. The use of a planetary-type mixer is preferred.

The method of manufacturing the solid naproxen concentrate optionally can contain a step of drying the naproxen concentrate. The wet naproxen concentrate can be dried directly or after a sieving step. Preferably, the wet naproxen concentrate is sieved (e.g., through a 10-40 mesh screen) before drying. Drying of the naproxen concentrate can be achieved by any suitable manner, such as by forced air ovens, convection ovens, or fluid bed driers. Drying is complete when the naproxen concentrate moisture content is about 0.1 to about 5% (e.g., about 0.2%, about 0.5%, about 0.7%, about 1%, about 1.2%, about 1.5%, about 1.7%, about 2%, about 2.2%, about 2.5%, about 2.7%, about 3%, about 3.2%, about 3.5%, about 3.7%, about 4%, about 4.2%, about 4.5%, about 4.7%, and ranges thereof). Preferably, the naproxen concentrate moisture content is about 0.2% to about 3%, and more preferably about 0.2% to about 2%.

Without being bound by any particular mechanism, the transformation process of naproxen salt (low density powder of small particle size) into naproxen concentrate (high density solid of larger particle size) involves an initial surface reaction between the acid solution and the solid naproxen salt. The reaction generates the alkali salt of the acidic substance, which upon drying, forms solid bridges between the surfaces of the drug particles and changes the dissolution rate. Based on the molar ratio and type of the acid used, different rates of release can be obtained. If hydrophilic or water-soluble acids are used, the in-situ salt provides a hydrophilic surface and osmotic material that enhances the wettability of the drug particles and the penetration of water into those particles and increases the drug dissolution rate. When less hydrophilic acids, such as short or medium chain fatty acids, are used, the in-situ salt results in controlled release mixtures.

Dried naproxen concentrates have improved physical properties compared to naproxen salts or naproxen free acid. Naproxen concentrates have a higher bulk density, larger particle size, better compressibility, and a reduced amount of fines as compared to naproxen powder. These advantages make the naproxen concentrates of the invention an exceptional material for making solid dosage forms, such as tablets and capsules, where easier processing and better quality finished products can be achieved while minimizing the number and amount of added adjuvants and/excipients.

The solid naproxen concentrate can have any suitable bulk density. Preferably, the bulk density of the solid naproxen concentrate is at least about 0.3 g/mL (e.g., at least about 0.35 g/mL, at least about 0.4 g/mL, at least about 0.45 g/mL, at least about 0.5 g/mL, at least about 0.55 g/mL, at least about 0.6 g/mL, at least about 0.65 g/mL, at least about 0.7 g/mL, at least about 0.75 g/mL, at least about 0.8 g/mL, at least about 0.9 g/mL, at least about 1 g/mL, at least about 1.25 g/mL, at least about 1.5 g/mL, or at least about 2 g/mL).

The composition (e.g., pharmaceutical composition) comprising the solid naproxen concentrate also can contain one or more carriers or excipients. The carriers or excipients must be acceptable in the sense of being compatible with the other ingredients and not deleterious to the recipient thereof. Examples of carriers or excipients for oral administration include cornstarch, lactose, magnesium stearate, talc, microcrystalline cellulose, stearic acid, povidone, crospovidone, dibasic calcium phosphate, sodium starch glycolate, hydroxypropyl cellulose (e.g., low substituted hydroxypropyl cellulose), hydroxypropylmethyl cellulose (e.g., hydroxypropylmethyl cellulose 2910), and sodium lauryl sulfate.

The naproxen concentrates of the invention can be formulated into soft gelatin capsules (softgel capsules). Although classified as a solid dosage form, soft gelatin capsules offer a unit-dose liquid dosage encapsulated in an edible shell.

To formulate softgel capsules, the naproxen concentrate is dissolved in a softgel capsule vehicle. Any suitable softgel capsule vehicle can be used. Examples of softgel capsule vehicles include water, polyethylene glycol, polyoxyl castor oil (Cremophor EL), polyoxyethylene sorbitan monooleate (Polysorbate 80), caprylocaproyl macrogol-8 glyceride (Labrasol), absolute alcohol, Poloxamer 124 (ethylene oxide/propylene oxide block copolymer), triethyl citrate (TEC), glycerin, polyvinyl pyrrolidone (PVP K-17), and mixtures thereof. Preferred combinations of vehicles include polyethylene glycol and polyoxyethylene sorbitan monooleate, polyoxyl castor oil, water, or Poloxamer 124.

Polyethylene glycol having any suitable molecular weight can be used in the softgel capsule vehicle. Typically, the polyethylene glycol has a molecular weight of 300 to 1500, preferably a molecular weight of 400 to 600, and more preferably a molecular weight of 400. Polyethylene glycol 400 (PEG 400) can be supplied by Dow Chemical under the trade name Carbowax® Sentry® super refined PEG 400. Typically, the water is purified when used in the softgel capsule vehicle.

The naproxen concentrates are soluble in soft capsule vehicles, such as polyethylene glycol, without the need of adding surfactants, hydrophilic polymers, or hydroxides, the addition of which decreases the naproxen concentration. Additionally, unlike some existing techniques, the dissolution of the naproxen concentrates in the soft capsule vehicles, such as polyethylene glycol, does not require excessive heating for a long time, which can cause drug degradation and/or interaction with the vehicle, forming polyethylene glycol-naproxen esters.

The softgel fills can be encapsulated into soft gelatin capsules using any suitable mechanism known in the art, such as rotary die technology (see J. P. Stanley, in The Theory and Practice of industrial Pharmacy; Lachman et al., Ed., Philadelphia, 1976).

The gelatin shell can be from any suitable source, such as bovine, porcine, fish, or poultry origin.

The gelatin shell can be of any suitable bloom strength, such as about 100 to about 250 bloom (e.g., about 125 bloom, about 150 bloom, about 175 bloom, about 200 bloom, about 225 bloom), and preferably about 150 bloom.

The gelatin shell can be plasticized with tri- or polyalcoholic plasticizers, such as glycerin, sorbitol, xylitol, or mixtures thereof. A mixture of glycerol and sorbitol is preferred.

The softgel capsules can have any suitable moisture content, such as a total moisture content of less than 10% (e.g., less than about 9%, less than about 8%, less than about 7%, less than about 6%, less than about 5%, or ranges thereof), and preferably less than about 7%.

The invention includes other oral pharmaceuticals manufactured from the naproxen concentrate, such as hard shell capsules. Hard shell capsules can be produced by filling the naproxen concentrate of the invention into two piece capsules. The two piece capsules also can include lubricants and disintegrating agents as known in the art.

Additionally, the naproxen concentrate can be used to formulate immediate or controlled release naproxen-containing tablets and capsules, using standard techniques.

The invention also provides liquid oral pharmaceuticals manufactured from the naproxen concentrate, such as liquid suspensions and solutions, drops, and syrups. Liquid oral pharmaceuticals can be prepared by directly dissolving naproxen concentrates into a hydrophilic vehicle or a mixture of hydrophilic vehicles, such as water, propylene glycol, and glycerol.

Other adjuvants, such as sweeteners, flavor-enhancing agents, taste masking agents, anti-microbial preservatives, or viscosity imparting agents, can also be used in the pharmaceuticals as known in the art.

Suitable sweeteners include, for example, saccharin sodium, sucrose, sorbitol, aspartame, and mannitol, or mixtures thereof.

Suitable flavoring agents include grape flavor, cherry flavor, cotton candy flavor, or other suitable flavor to make the liquid pharmaceutical easier for a patient to ingest. The flavoring agent or mixtures thereof are typically present in an amount of from about 0.0001 wt % to about 5 wt %.

Suitable anti-microbial preservatives include, for example, methylparaben, propylparaben, sodium benzoate, benzalkonium chloride, or mixtures thereof. The preservative or mixtures thereof are typically present in an amount of from about 0.0001 wt % to about 2 wt %.

Alternatively, naproxen concentrates can be used as powder for re-constitution with one or more adjuvants.

The naproxen concentrates of the invention can be formulated into oral pharmaceuticals at any suitable dose. For example, the naproxen concentrates can be formulated into solid dosage forms with naproxen dosages of 50 mg, 100 mg, 200 mg, 300 mg, 400 mg, 500 mg, 600 mg, 700 mg, 800 mg, 900 mg, 1,000 mg, and ranges thereof. For example, the naproxen concentrates can be formulated into a tablet containing the equivalent of about 200 mg to about 800 mg naproxen per tablet. The naproxen concentrates also can be formulated into a hard shell or soft shell capsule containing the equivalent of about 200 mg to about 500 mg per capsule.

The naproxen concentrates also can be formulated into liquid suspensions or solutions at any suitable naproxen dose. Generally, the liquid concentrates can be formulated with naproxen concentrations of 1 mg/mL to 1000 mg/mL (e.g., 10 mg/mL, 20 mg/mL, 30 mg/mL, 40 mg/mL, 50 mg/mL, 60 mg/mL, 80 mg/mL, 100 mg/mL, 200 mg/mL, 300 mg/mL, 500 mg/mL, 550 mg/mL, 700 mg/mL, 800 mg/mL, and ranges thereof). Preferably, the liquid concentrates have naproxen concentrates of 10 mg/mL to about 500 mg/mL, and more preferably 20 mg/mL to 40 mg/mL.

The following examples further illustrate the invention but, of course, should not be construed as in any way limiting its scope.

Example 1

This example demonstrates the preparation of a solid naproxen concentrate of the invention.

85.20 g of naproxen concentrate was prepared using the following ingredients.

| Ingredient | Amount (g) |
| --- | --- |
| Naproxen sodium, USP | 75.60 |
| Citric acid, USP | 9.60 |

Naproxen sodium was dry-mixed with citric acid in planetary (Hobart) mixer for 5 min. The blend was mixed with purified water (18.00 g) for 5 min, and the wet mass was dried at 45°±5° C. in a drying oven for 8 hours. Dried naproxen concentrate then was screened through #30 mesh screen.

The resultant naproxen concentrate had final moisture content of 2.2% and bulk density of 0.41 g/mL.

Example 2

This example demonstrates the preparation of a solid naproxen concentrate of the invention.

28.50 g of naproxen concentrate was prepared using the following ingredients.

| Ingredient | Amount (g) |
| --- | --- |
| Naproxen sodium, USP | 25.20 |
| Hydrochloric acid, NF | 3.50 |

Naproxen sodium was dry-mixed with citric acid in planetary (Hobart) mixer for 5 min. The blend was mixed with purified water (10.00 g) for 5 min, and the wet mass was dried at 45°±5° C. in a drying oven. Dried naproxen concentrate then was screened through #30 mesh screen.

The resultant naproxen concentrate had final moisture content of 2.2% and bulk density of 0.41 g/mL.

Example 3

This example demonstrates the preparation of a solid naproxen concentrate of the invention.

146.00 g of naproxen concentrate was prepared using the following ingredients.

| Ingredient | Amount (g) |
| --- | --- |
| Naproxen sodium, USP | 100.00 |
| Maleic acid (Hydroxysuccinic acid) | 46.00 |

Naproxen sodium was dry-mixed with maleic acid in planetary (Hobart) mixer for 5 min. The blend was mixed with purified water (28.00 g) for 5 min, and the wet mass was dried at 45°±5° C. in a drying oven. Dried naproxen concentrate then was screened through #30 mesh screen.

The resultant naproxen concentrate had final moisture content of 1.82% and bulk density of 0.45 g/mL.

Example 4

This example demonstrates the preparation of a solid naproxen concentrate of the invention.

40.00 g of naproxen concentrate was prepared using the following ingredients.

| Ingredient | Amount (g) |
| --- | --- |
| Naproxen sodium, USP | 25.00 |
| Tartaric acid, USP | 15.00 |

Naproxen sodium was dry-mixed with tartaric acid in planetary (Hobart) mixer for 5 min. The blend was mixed with purified water (15.00 g) for 5 min, and the wet mass was dried at 45°±5° C. in a drying oven. Dried naproxen concentrate then was screened through #30 mesh screen.

The resultant naproxen concentrate had final moisture content of 2.2% and bulk density of 0.38 g/mL.

Example 5

This example demonstrates the preparation of a solid naproxen concentrate of the invention.

120.00 g of naproxen concentrate was prepared using the following ingredients.

| Ingredient | Amount (g) |
| --- | --- |
| Naproxen sodium, USP | 100.00 |
| Lactic acid (2-hydroxypropanoic acid) | 20.00 |

Naproxen sodium was mixed with lactic acid solution for 5 min. Purified water (360.00 g) was added, and the wet mass was dried at 45°±5° C. in a drying oven for 72 hours. Dried naproxen concentrate then was screened through #30 mesh screen.

The resultant naproxen concentrate had final moisture content of 4.50% and bulk density of 0.52 g/mL.

Example 6

This example demonstrates the preparation a solid naproxen concentrate of the invention.

5983.60 g of naproxen concentrate was prepared using the following ingredients.

| Ingredient | Amount (g) |
| --- | --- |
| Naproxen sodium, USP | 4983.60 |
| Lactic acid (2-hydroxypropanoic acid) | 1000.00 |

Naproxen sodium was mixed with lactic acid solution for 5 min. Purified water (1794.00 g) was added, and the wet mass was dried at 45°±5° C. in a drying oven for 92 hours. Dried naproxen concentrate then was screened through #30 mesh screen.

The resultant naproxen concentrate had final moisture content of 4.0% and bulk density of 0.52 g/mL.

Example 7

This example demonstrates the preparation a solid naproxen concentrate of the invention.

A 50.0 kg batch of naproxen concentrate was prepared using the following ingredients.

| Ingredient | Amount (kg) |
| --- | --- |
| Naproxen sodium, USP | 41.644 |
| Lactic acid (2-hydroxypropanoic acid) | 8.356 |

Naproxen sodium was mixed with lactic acid solution for 10 min. Purified water (14.989 kg) was added, and the wet mass was dried at 45°±5° C. in a drying oven for 72 hours. Dried naproxen concentrate then was screened through #30 mesh screen.

The resultant naproxen concentrate had final moisture content of 3.8% and bulk density of 0.61 g/mL.

Example 8

This example demonstrates the preparation of a solution of the solid naproxen concentrate.

18.0 kg of naproxen sodium soft gelatin capsules fill material was prepared using the following ingredients.

| Ingredient | Amount (kg) |
| --- | --- |
| Naproxen concentrate from Example 6 | 5.471 |
| Polyethylene Glycol 400, NF | 9.469 |
| Purified Water, USP | 1.260 |
| Polyvinyl pyrrolidone, PVP K-17 | 0.900 |
| Propylene glycol, USP | 0.900 |

Naproxen concentrate was dissolved in a polyethylene glycol 400/purified water/polyvinyl pyrrolidone K-17/propylene glycol mixture at 45° C.±5° C. The solution was cooled to room temperature and deaerated using a vacuum. The resultant fill material was clear. Each 0.90 g of fill material contained 220.0 mg naproxen sodium.

Example 9

This example demonstrates the preparation of a solution of the solid naproxen concentrate.

67.5 kg of naproxen sodium soft gelatin capsules fill material was prepared using the following ingredients.

| Ingredient | Amount (kg) |
| --- | --- |
| Naproxen concentrate from Example 7 | 20.518 |
| Polyethylene Glycol 400, NF | 35.507 |
| Purified Water, USP | 4.725 |
| Polyvinyl pyrrolidone, PVP K-17 | 3.375 |
| Propylene glycol, USP | 3.375 |

Naproxen concentrate was dissolved in a polyethylene glycol 400/purified water/polyvinyl pyrrolidone K-17/propylene glycol mixture at 45° C.±5° C. The solution was cooled to room temperature and deaerated using a vacuum. The resultant fill material was clear. Each 0.90 g of fill material contained 220.0 mg naproxen sodium.

Example 10

This example demonstrates the preparation of a solution of the solid naproxen concentrate.

99.0 kg of naproxen sodium soft gelatin capsules fill material was prepared using the following ingredients.

| Ingredient | Amount (kg) |
| --- | --- |
| Naproxen concentrate from Example 7 | 30.292 |
| Polyethylene Glycol 400, NF | 51.878 |
| Purified Water, USP | 6.930 |
| Polyvinyl pyrrolidone, PVP K-17 | 4.950 |
| Propylene glycol, USP | 4.950 |

Naproxen concentrate was dissolved in a polyethylene glycol 400/purified water/polyvinyl pyrrolidone K-17/propylene glycol mixture at 45° C.±5° C. The solution was cooled to room temperature and deaerated. The resultant fill material was clear. Each 0.90 g of fill material contained 220.0 mg naproxen sodium.

Example 11

This example demonstrates the formulation of the naproxen concentrate into an oral pharmaceutical form.

The fill material of Example 8 was encapsulated into 18 oblong soft gelatin capsules using Bochang rotary die encapsulator and 200 bloom, limed bone, Type B, gelatin plasticized with polyols, using conventional methods (see, e.g., Wilkinson et al., "Softgels: Manufacturing considerations," Drugs and the Pharmaceutical Sciences, 41 (Specialized Drug Delivery Systems), P. Tyle, Ed. (Marcel Dekker, Inc., New York, 1990) pp. 409-449; Hom et al., "Capsules, Soft," Encyclopedia of Pharmaceutical Technology, Vol 2, J. Swarbrick and J. C. Boylan, eds. (Marcel Dekker, Inc., New York, 1990) pp 260-284; Patel et al., *Manufacturing Chemist*, 60(7): 26-28 (1989); Patel et al., *Manufacturing Chemist*, 60(8): 47-49 (1989); Jimerson et al., *Drug Development and Industrial Pharmacy*, 12(8-9): 1133-1144 (1986); and Ebert, *Pharmaceutical Technology*, 1(5):44-50 (1977)).

Example 12

This example demonstrates the formulation of the naproxen concentrate into an oral pharmaceutical form.

The fill material of Example 8 was encapsulated into 20 oblong soft gelatin capsules using Bochang rotary die encapsulator and 200 bloom, limed bone, Type B, gelatin plasticized with polyols, using conventional methods.

Example 13

This example demonstrates the formulation of the naproxen concentrate into an oral pharmaceutical form.

The fill material of Example 9 was encapsulated into 20 oblong soft gelatin capsules using Bochang rotary die encapsulator and 200 bloom, limed bone, Type B, gelatin plasticized with polyols, using conventional methods.

Example 14

This example demonstrates the formulation of the naproxen concentrate into an oral pharmaceutical form.

The fill material of Example 10 was encapsulated into 20 oblong soft gelatin capsules using Bochang rotary die encapsulator and 200 bloom, limed bone, Type B, gelatin plasticized with polyols, using conventional methods.

Example 15

This example demonstrates the stability of the inventive naproxen concentrate.

The fill material of Example 8 was charged for stability at 30° C. and 65% relative humidity (RH) and long term temperature 25° C. and 65% RH for 6 months. The fill material showed potency of 99% and related compounds at less than 0.1%. Furthermore, capsules containing the fill material had no physical defects.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition consisting essentially of a solid naproxen concentrate, wherein the solid naproxen concentrate consists of (a) a solid naproxen free acid, (b) a solid naproxen alkali salt, and (c) at least one acidic substance selected from the group consisting of lactic acid, gluconic acid, citric acid, tartaric acid, hydrochloric acid, phosphoric acid, nitric acid, sulfuric acid, maleic acid, monosodium citrate, disodium citrate, potassium citrate, monosodium tartrate, disodium tartrate, potassium tartrate, aspartic acid, carboxy-methylcellulose, acrylic polymers, methacrylic polymers, and mixtures thereof, wherein at least 90% of the weight of the solid naproxen concentrate is naproxen free acid and naproxen alkali salt, and wherein the solid naproxen concentrate does not comprise one or more binders.

2. The composition of claim 1, wherein at least 92% of the weight of the solid naproxen concentrate is naproxen free acid and naproxen alkali salt.

3. The composition of claim 1, wherein at least 95% of the weight of the solid naproxen concentrate is naproxen free acid and naproxen alkali salt.

4. The composition of claim 1, wherein at least 97% of the weight of the solid naproxen concentrate is naproxen free acid and naproxen alkali salt.

5. The composition of claim 1, wherein the composition is a hard shell capsule, soft gelatin capsule, liquid suspension, liquid solution, or tablet.

6. The composition of claim 5, wherein the composition is a tablet.

7. The composition of claim 6, equivalent to about 200 to about 1000 mg naproxen per tablet.

8. The composition of claim 1, wherein the solid naproxen alkali salt is selected from the group consisting of naproxen sodium salt, naproxen potassium salt, naproxen ammonium salt, and mixtures thereof.

9. A pharmaceutical formulation comprising (a) a solid naproxen concentrate, wherein the solid naproxen concentrate consists of a solid naproxen free acid, a solid naproxen alkali salt, and at least one acidic substance selected from the group consisting of lactic acid, gluconic acid, citric acid, tartaric acid, hydrochloric acid, phosphoric acid, nitric acid, sulfuric acid, maleic acid, monosodium citrate, disodium citrate, potassium citrate, monosodium tartrate, disodium tartrate, potassium tartrate, aspartic acid, carboxy-methylcellulose, acrylic polymers, methacrylic polymers, and mixtures thereof, wherein at least 90% of the weight of the solid naproxen concentrate is naproxen free acid and naproxen alkali salt, and wherein the solid naproxen concentrate does not comprise one or more binders; and (b) a pharmaceutically acceptable carrier.

10. The composition of claim 9, wherein at least 92% of the weight of the solid naproxen concentrate is naproxen free acid and naproxen alkali salt.

11. The composition of claim 9, wherein at least 95% of the weight of the solid naproxen concentrate is naproxen free acid and naproxen alkali salt.

12. The composition of claim 9, wherein at least 97% of the weight of the solid naproxen concentrate is naproxen free acid and naproxen alkali salt.

13. The composition of claim 9, wherein the composition is a hard shell capsule, soft gelatin capsule, liquid suspension, liquid solution, or tablet.

14. The composition of claim 13, wherein the composition is a tablet.

15. The composition of claim 14, equivalent to about 200 to about 1000 mg naproxen per tablet.

16. The composition of claim 9, wherein the solid naproxen alkali salt is selected from the group consisting of naproxen sodium salt, naproxen potassium salt, naproxen ammonium salt, and mixtures thereof.

17. A method of manufacturing a solid naproxen concentrate, wherein at least 90% of the weight of the naproxen concentrate is naproxen free acid and naproxen alkali salt, comprising: (a) mixing a naproxen alkali salt with at least one acidic substance selected from the group consisting of lactic acid, gluconic acid, citric acid, tartaric acid, hydrochloric acid, phosphoric acid, nitric acid, sulfuric acid, maleic acid, monosodium citrate, disodium citrate, potassium citrate, monosodium tartrate, disodium tartrate, potassium tartrate, aspartic acid, carboxy-methylcellulose, acrylic polymers, methacrylic polymers, and mixtures thereof, to form a composition; and (b) optionally drying the composition to produce a solid naproxen concentrate.

18. The method of claim 17, wherein the at least one acidic substance is in the form of an aqueous or hydroalcoholic solution.

19. The method of claim 18, further comprising sieving the composition prior to drying.

20. The method of claim 19, further comprising adding water or a water-miscible solvent to the composition.

21. The method of claim 19, further comprising filling the solid naproxen concentrate in hard shell capsules.

22. A method of preparing a soft gelatin capsule formulation comprising: (a) providing a solid naproxen concentrate consisting of a solid naproxen free acid, a solid naproxen alkali salt, and at least one acidic substance selected from the group consisting of lactic acid, gluconic acid, citric acid, tartaric acid, hydrochloric acid, phosphoric acid, nitric acid, sulfuric acid, maleic acid, monosodium citrate, disodium citrate, potassium citrate, monosodium tartrate, disodium tartrate, potassium tartrate, aspartic acid, carboxy-methylcellulose, acrylic polymers, methacrylic polymers, and mixtures thereof, wherein at least 90% of the weight of the solid naproxen concentrate is naproxen free acid and naproxen alkali salt, and wherein the solid naproxen concentrate does not comprise one or more binders; (b) dissolving the solid naproxen concentrate in a soft gelatin capsule vehicle to form a soft gelatin fill; and (c) encapsulating the soft gelatin fill in a soft gelatin capsule; thereby preparing a soft gelatin capsule formulation.

23. The method of claim 22, wherein the soft gelatin capsule vehicle is polyethylene glycol.

24. A composition consisting essentially of a solid naproxen concentrate, wherein the solid naproxen concentrate consists of (a) a solid naproxen free acid, (b) a solid naproxen alkali salt, and (c) and at least one acidic substance selected from the group consisting of lactic acid, gluconic acid, citric acid, tartaric acid, hydrochloric acid, phosphoric acid, nitric acid, sulfuric acid, maleic acid, monosodium citrate, disodium citrate, potassium citrate, monosodium tartrate, disodium tartrate, potassium tartrate, aspartic acid, carboxy-methylcellulose, acrylic polymers, methacrylic polymers, and mixtures thereof, and wherein at least 90% of the weight of the solid naproxen concentrate is naproxen free acid and naproxen alkali salt, wherein the naproxen free acid is produced from a solid naproxen alkali salt using at least one acidic substance selected from the group consisting of lactic acid, gluconic acid, citric acid, tartaric acid, hydrochloric acid, phosphoric acid, nitric acid, sulfuric acid, maleic acid, monosodium citrate, disodium citrate, potassium citrate, monosodium tartrate, disodium tartrate, potassium tartrate, aspartic acid, carboxy-methylcellulose, acrylic polymers, methacrylic polymers, and mixtures thereof, and wherein the solid naproxen concentrate does not comprise one or more binders.

25. The composition of claim 24, wherein at least 95% of the weight of the solid naproxen concentrate is naproxen free acid and naproxen alkali salt.

26. The composition of claim 24 wherein the composition is a hard shell capsule, soft gelatin capsule, liquid suspension, liquid solution, or tablet.

* * * * *